United States Patent [19]

Ives

[11] Patent Number: 5,445,162
[45] Date of Patent: Aug. 29, 1995

[54] APPARATUS AND METHOD FOR RECORDING AN ELECTROENCEPHALOGRAM DURING MAGNETIC RESONANCE IMAGING

[75] Inventor: John R. Ives, Lexington, Mass.
[73] Assignee: Beth Israel Hospital Association, Brookline, Mass.
[21] Appl. No.: 113,785
[22] Filed: Aug. 27, 1993
[51] Int. Cl.⁶ ............................................. A61B 5/0478
[52] U.S. Cl. .................. 128/731; 128/653.2
[58] Field of Search ................. 128/731–732, 128/653.1–653.2, 644; 607/9

[56] References Cited

U.S. PATENT DOCUMENTS

| | | | |
|---|---|---|---|
| 4,736,751 | 4/1988 | Gevins et al. | 128/731 X |
| 4,949,725 | 8/1990 | Raviv et al. | 128/731 |
| 4,951,674 | 8/1990 | Zanakis et al. | 128/731 X |
| 4,974,602 | 12/1990 | Abraham-Fuchs et al. | 128/731 |
| 5,119,816 | 6/1992 | Gevins | 128/644 |
| 5,159,929 | 11/1992 | Morris et al. | 128/653.2 |
| 5,217,010 | 6/1993 | Tsitlik et al. | 607/9 |
| 5,220,921 | 6/1993 | Ferris et al. | 128/731 X |
| 5,269,315 | 12/1993 | Levchter et al. | 128/731 |
| 5,323,776 | 6/1994 | Blakeley et al. | 128/653.2 X |

FOREIGN PATENT DOCUMENTS

WO/92/212-81  5/1992  WIPO ............... 128/653.2

Primary Examiner—Angela D. Sykes
Attorney, Agent, or Firm—Wolf, Greenfield & Sacks

[57] ABSTRACT

A method and apparatus for recording an electroencephalogram (EEG) during magnetic resonance imaging (MRI). Nonmagnetic electrodes are attached to a patient's scalp. EEG signals are multiplexed, amplified, and transmitted to an EEG machine or a personal computer located outside the MRI room. By reducing the amount of magnetic metal and radio frequency generating equipment associated with the recording of the EEG that is within the bore of the MRI magnet, and moving all significant radio frequency generating equipment outside the MRI room, EEG signals can be recorded and MRI images can be obtained simultaneously. The EEG signals are analyzed and, in response to a predetermined pattern, the MRI machine is triggered.

36 Claims, 4 Drawing Sheets

APPARATUS AND METHOD FOR RECORDING AN ELECTROENCEPHALOGRAM DURING MAGNETIC RESONANCE IMAGING

FIELD OF THE INVENTION

This invention relates to the recording of an electroencephalogram (EEG) during magnetic resonance imaging (MRI). The activity of the EEG can be used to acquire MRI images and thus correlate neurophysiological phenomena with the results.

BACKGROUND OF THE INVENTION

An EEG machine permits the recording of specific brain wave patterns in a patient. An MRI machine can provide metabolic and anatomical information regarding a portion of a patient, including a portion of the patient's brain. However, in the prior art, it has not been possible to record an EEG pattern at the same time that MRI is conducted. This prevents the obtaining of metabolic and anatomical information that is correlated to particular neurophysiological waveforms being studied. By obtaining such a correlation, it would be possible to obtain increased information regarding abnormal as well as normal brain activity and to obtain a better understanding of the functioning of the brain.

The nature of the MRI and EEG severely restrict the ability to record the EEG during magnetic resonance imaging. For example, the strong and rapidly changing radio frequency fields present during MRI, coupled with the large static magnetic field, may induce significant current flow in electrodes and wires located within the magnetic field. When conducting an EEG, the electrodes are connected to a patient's scalp, where the current may produce localized heating or burns.

Also, the equipment necessary to obtain the EEG can interfere with the diagnostic quality of the MRI images. This occurs both because the electrodes produce artifacts on the MRI images and because any radio frequency sources associated with the EEG equipment will interfere with the MRI images.

In addition, the radio frequency and magnetic fields can compromise the quality of the EEG or even make it impossible to obtain.

Currently, patients receiving an MRI who also are having their EEG recorded generally will have the EEG electrodes removed before there are placed in the MRI machine. In some cases, the electrodes are left in place during an MRI, but those electrodes have caused artifacts on the MRI image and it has not been possible to record the EEG during the MRI process.

It is therefore an object of the present invention to provide a method and apparatus for obtaining an EEG during magnetic resonance imaging.

It is another object of the present invention to provide a method and apparatus for triggering an MRI image in response to specific EEG signal patterns.

SUMMARY OF THE INVENTION

By reducing the amount of magnetic metal and radio frequency generating equipment associated with the recording of the EEG that is within the bore of the MRI magnet, and moving all significant radio frequency generating equipment outside the MRI room, EEG signals can be recorded and MRI images can be obtained simultaneously.

According to the present invention, the above and other objects and advantages are achieved by positioning a plurality of nonmagnetic electrodes on a patient's head so as to be able to record the patient's EEG. In a preferred embodiment, these can include, surface electrodes having a surface of gold or silver, and sphenoidal electrodes made of Teflon-coated silver wire. A plurality of EEG signals from the electrodes are transmitted to an amplifier that is positioned sufficiently away from the patient's head so as to prevent distortion of the MRI. Preferably, this distance is at least five centimeters. In a preferred embodiment, electrode extension cables are used so as to position the amplifier outside the bore of the MRI magnet. In a preferred embodiment, the plurality of EEG signals are also multiplexed. This can be done with a combined amplifier/multiplexor unit.

The amplified EEG signals are transmitted to an EEG machine or a personal computer, where they are recorded. In a preferred embodiment the amplified, multiplexed signals are first sent through a signal splitter. One output of the signal splitter is fed to a demultiplexor and into the EEG machine, and another output of the signal splitter is fed to the personal computer. The EEG machine can be either within or outside the MRI room. The personal computer is located outside the MRI room.

In a preferred embodiment, the personal computer can be used to analyze the signals and, in response to appropriate EEG patterns, trigger the MRI. Alternatively, the MRI may be triggered manually in response to a visual inspection of the EEG patterns.

BRIEF DESCRIPTION OF THE DRAWINGS

For a better understanding of the present invention, together with other and further objects, advantages, and capabilities thereof, reference is made to the accompanying drawings which are incorporated herein by reference and in which:

In FIGS. 1-3, like elements have the same reference numbers.

DETAILED DESCRIPTION OF THE INVENTION

Figure 1:
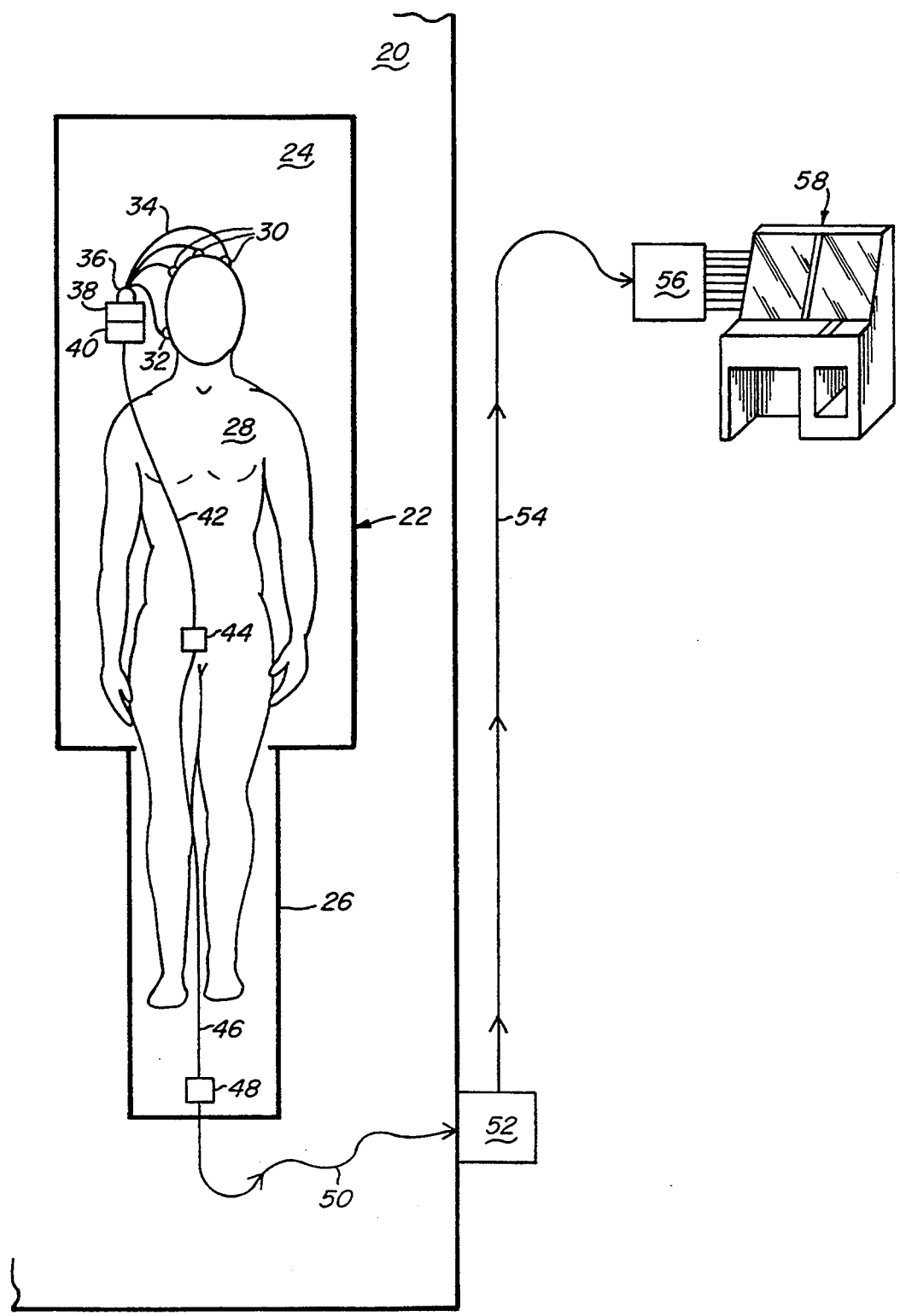
FIG. 1 is a schematic diagram of the method for obtaining an EEG during magnetic resonance imaging in accordance with the invention.

With reference to FIG. 1, an MRI room 20 contains an MRI machine 22 in which extends a bore of MRI magnet 24. MRI room 20 also contains a moving table 26 on which a patient 28 rests. In a preferred embodiment, the MRI machine 22 is a Siemens 1.5 T whole body scanner with hardware modifications to provide echo planar capabilities.

Figure 2:
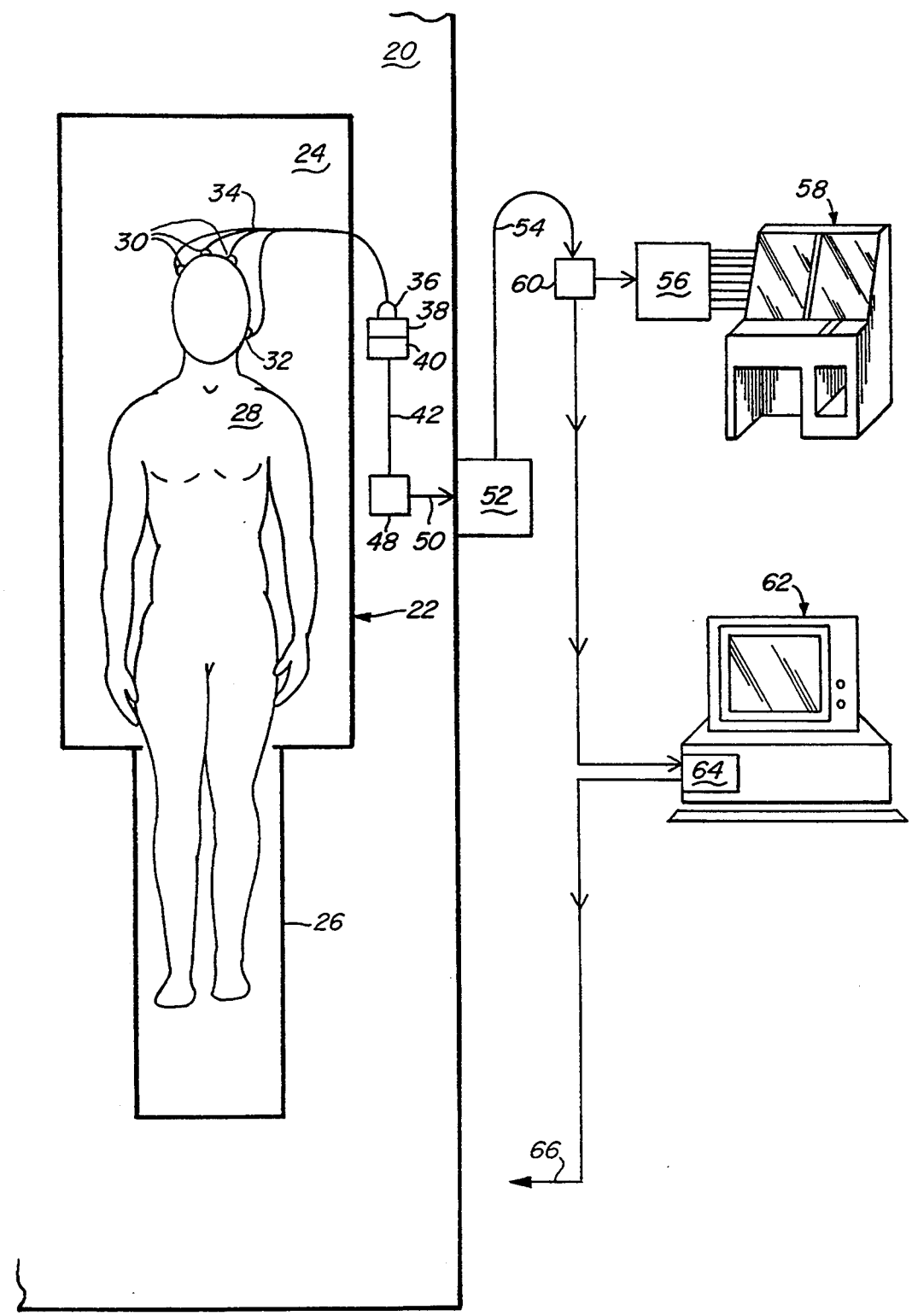
FIG. 2 is a schematic diagram of an alternative method for obtaining an EEG during magnetic resonance imaging in accordance with the invention.

Surface electrodes 30 and sphenoidal electrodes 32 are positioned on the patient so as to permit the recording of the signals that make up the patient's EEG. In a preferred embodiment, the surface electrodes 30 are either Grass gold or silver electrodes, model numbers E5GH or E5SH, respectively; and the sphenoidal electrodes 32 are multi-stranded, Teflon-coated pure silver wire, such as Medwire part number AG 7/40T. Alternatively, only surface electrodes or only sphenoidal electrodes may be used, as appropriate. The surface electrodes 30 and sphenoidal electrodes 32 are connected to ribbon cabling 34, which is connected to a harness 36. Surface electrodes 30 and sphenoidal electrodes 32 are nonmagnetic. Preferably, ribbon cabling 34 also is nonmagnetic. Alternatively, the electrodes can be connected to the harness 36 by a length of wire, such as 25 mm standard Grass wire, or other electrode extension cables. The electrodes and cabling should be securely bandaged to the patient's head to minimize movement of the electrodes and cabling. The patient's head also should be secured as much as possible. Even slight movements due to pulsatile blood flow (ballistocardiogram) or movements of the head can cause artifacts to appear on the EEG. The harness 36 plugs into the inputs of a multiplexor 38, which multiplexes the multiple EEG signals onto a single line. Preferably, multiplexor 38 provides 18 channels and a sampling rate of 200 samples per second per channel. The output of multiplexor 38 is fed to amplifier 40. Multiplexor 38 and amplifier 40 can be situated in a single multiplexor/amplifier assembly. In a preferred embodiment, ribbon cabling 34 is at least five centimeters long, so the multiplexor 38 and amplifier 40 can be placed away from the head of the patient and avoid distortion of the MRI images. Preferably, ribbon cabling 34 is sufficiently long that multiplexor 38 and amplifier 40 can be positioned outside the bore of the MRI magnet 24 (FIG. 2).

As seen in FIG. 1, the output of amplifier 40 is transmitted along cable 42 to junction box 44, and from there along cable 46, to power pack 48. Power pack 48 is located outside the bore of the MRI magnet 24. Power pack 48 buffers the multiplexed EEG signals and supplies power and logic signals to multiplexor 38 and amplifier 40 through cable 46 and cable 42. Alternatively, cable 42 can be connected directly to power pack 48 (FIG. 2). This will occur where multiplexor 38 and amplifier 40 are located outside the bore of the MRI magnet 24, or where cable 42 has sufficient length. In such situations, junction box 44 and cable 46 can be omitted. Cable 50 connects power pack 48 to wall unit 52, which is located outside MRI room 20. Wall unit 52 further buffers the multiplexed EEG signals and supplies power to the power pack.

Alternatively, other suitable means can be used to transmit the amplified and multiplexed EEG signals from amplifier 40 to a point outside MRI room 20, and to provide the necessary power and logic signals to multiplexor 38 and amplifier 40.

Figure 3:
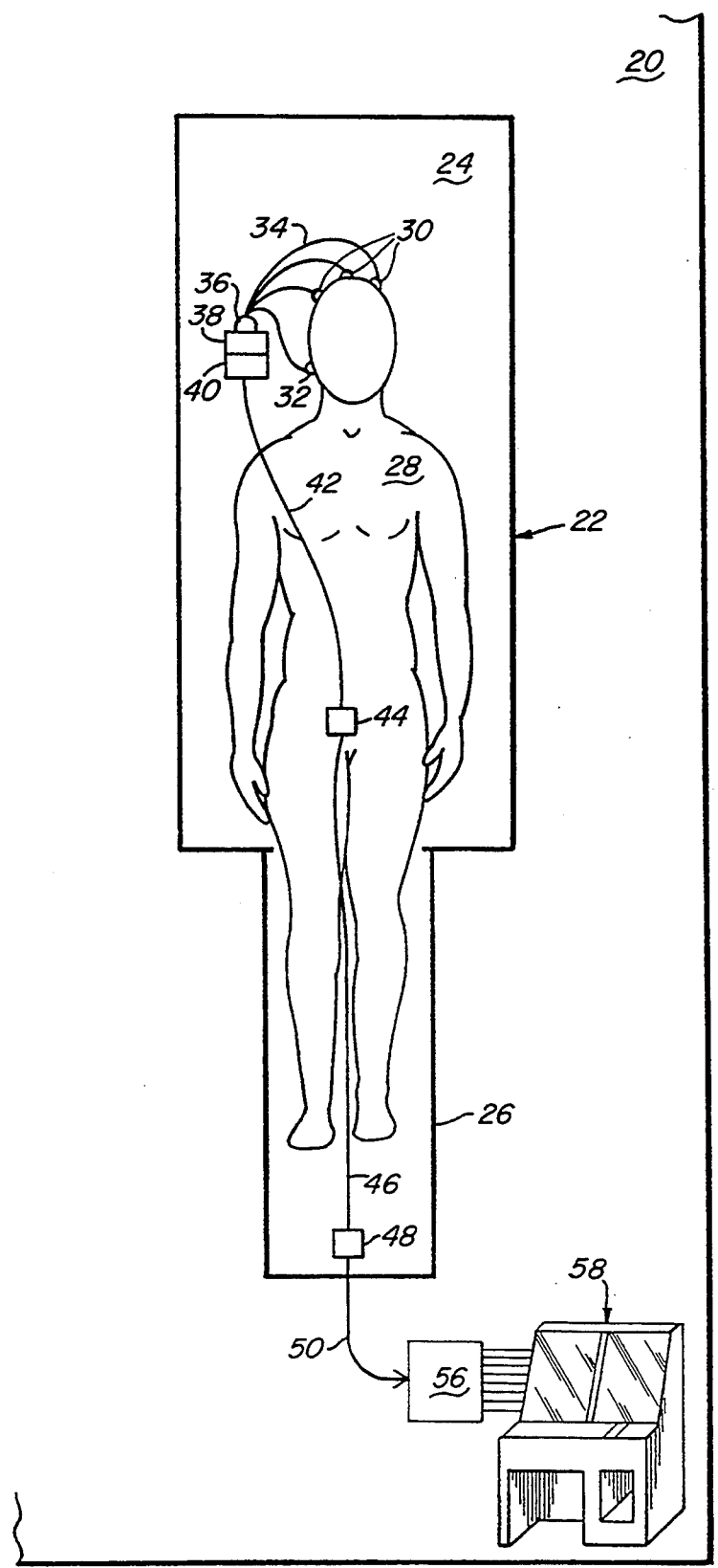
FIG. 3 is a schematic diagram of another alternative method for obtaining an EEG during magnetic resonance imaging in accordance with the invention.

Cable 54 is used to relay the EEG signals from wall unit 52 to demultiplexor 56, the output of which is connected to EEG machine 58 (FIG. 1). While in a preferred embodiment, EEG machine 58 is located outside MRI room 20, EEG machine 58 also can be located within MRI room 20, as shown in FIG. 3. Successful results with an EEG machine located within the MRI room were obtained with a Grass EEG machine model 8, which relies on analog technology. With this machine, unlike many machines based on digital technology, radio frequency fields that interfere with the operation of the MRI machine were not propagated.

In an alternative embodiment shown in FIG. 2, cable 54 can be connected to signal splitter 60. One output of signal splitter 60 is then fed through demultiplexor 56 to EEG machine 58, and a second output is fed to personal computer 62. Personal computer 62 utilizes an interface board 64 to translate the multiplexed EEG signal to digital signals that can be input into the computer. Personal computer 62 also records the patient's electrocardiogram (EKG), by receiving signals from EKG electrodes placed on the patient (not shown).

Personal computer 62 is used to analyze and store the EEG signals and the EKG signals, and to determine when to trigger MRI machine 22. Interface board 64 is used to generate MRI triggering signal 66. Alternatively, other signal processing equipment can be used instead of personal computer 62. Or, the EEG signals as viewed on a paper read-out or on a computer screen can be used to trigger manually the taking of an MRI image.

In operation, the plurality of EEG signals from patient 28 are picked up by surface electrodes 30 and sphenoidal electrodes 32. The EEG signals are transmitted by ribbon cabling 34 to harness 36, from where they are input into multiplexor 38. The output of multiplexor 38 is amplified by amplifier 40 and then transmitted to EEG machine 58 and/or personal computer 62. Personal computer 62 records the EEG data, as well as the patient's EKG, and also determines when to trigger MRI machine 22. Personal computer 62 causes interface board 64 to generate MRI triggering signal 66.

Figure 4:
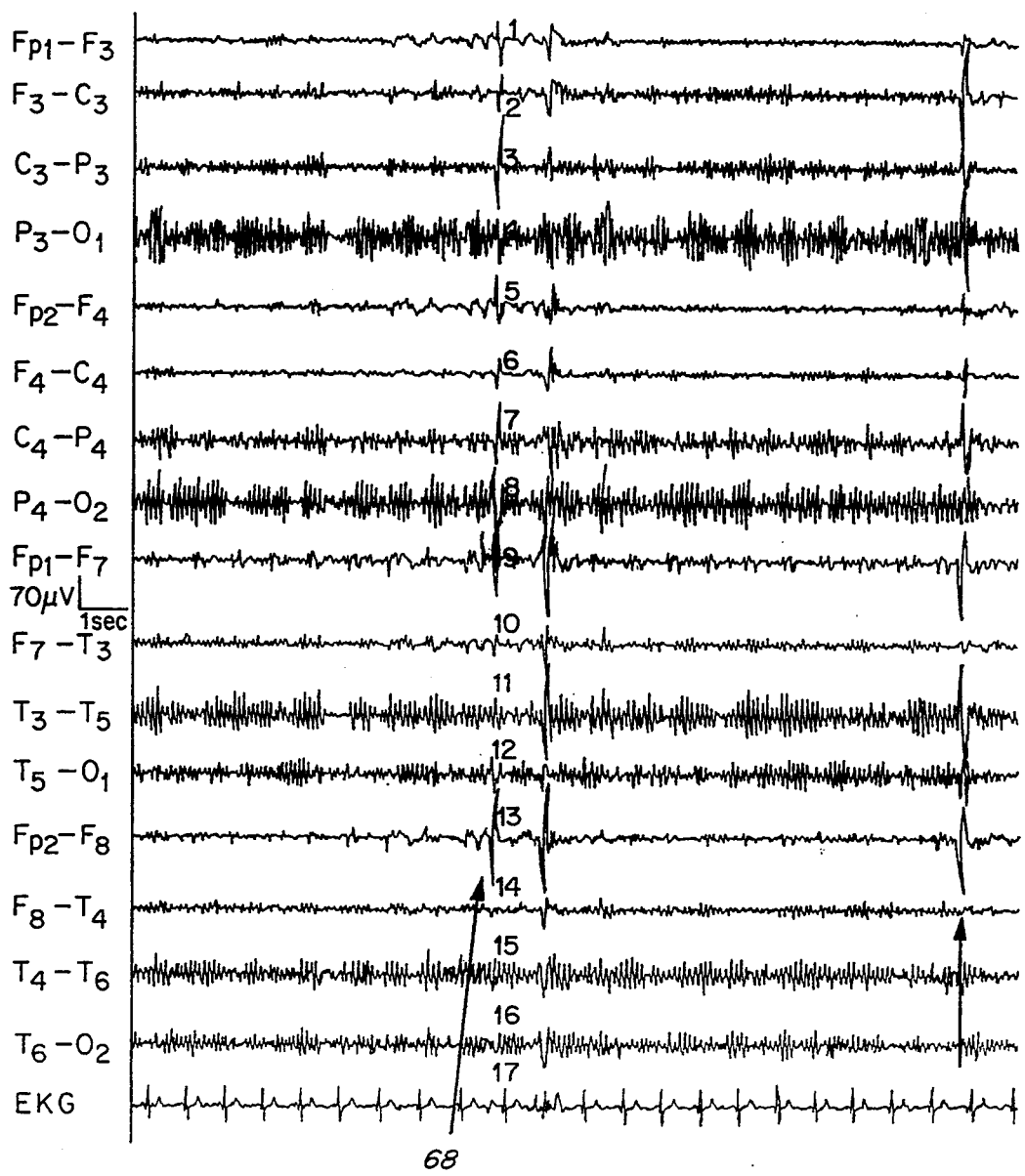
FIG. 4 is a graph of experimental data obtained by monitoring EEG signals of a patient during magnetic resonance imaging in accordance with one embodiment of the invention.

Recorded EEG data and EKG data are shown in FIG. 4. Although a momentary artifact is generated during acquisition of the echo planar scan by MRI machine 22, as can be seen at 68 in FIG. 4, the EEG data remains readable except during continuous spin echo scanning.

By repeatedly triggering on the same EEG pattern (as recognized by the personal computer or manually), numerous MRI slices can be obtained that correspond to the same brain wave pattern. By linking the MRI slices to a patient's cardiac cycle (by monitoring the patient's EKG), interference caused by background metabolic or anatomical changes associated with the cardiac cycle can be reduced. The use of nonmagnetic electrodes reduces injuries and discomfort to the patient and the appearance of artifacts on the MRI images, While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for obtaining an electroencephalogram during magnetic resonance imaging of a patient positioned in a magnetic resonance imaging room, comprising the steps of:
    placing a plurality of nonmagnetic electrodes on the patient's head so as to be able to record the patient's electroencephalogram;
    transmitting electroencephalogram signals from the plurality of electrodes to an amplifier; and
    recording the amplified electroencephalogram signals.

2. A method for obtaining an electroencephalogram during magnetic resonance imaging as defined in claim 1, wherein the recording step is conducted within the magnetic resonance imaging room.

3. A method for obtaining an electroencephalogram during magnetic resonance imaging as defined in claim 1, wherein the recording step is conducted outside of the magnetic resonance imaging room.

4. A method for obtaining an electroencephalogram during magnetic resonance imaging as defined in claim 1,
wherein the step of transmitting electroencephalogram signals from the plurality of electrodes to an amplifier comprises the steps of:
multiplexing the electroencephalogram signals; and
amplifying the multiplexed signals; and
wherein the step of recording the amplified signals comprises the steps of:
demultiplexing the amplified signals; and
supplying the demultiplexed signals to an electroencephalogram machine.

5. A method for obtaining an electroencephalogram during magnetic resonance imaging as defined in claim 1, wherein the amplifier is positioned at a sufficient distance from the patient's head to prevent distortion of the magnetic resonance imaging.

6. A method for obtaining an electroencephalogram during magnetic resonance imaging as defined in claim 5, wherein the amplifier is positioned at least five centimeters from the patient's head.

7. A method for obtaining an electroencephalogram during magnetic resonance imaging as defined in claim 1, further comprising the steps of: analyzing the recorded signals to determine an electroencephalogram signal pattern; and
triggering a magnetic resonance imaging machine when the electroencephalogram signal pattern corresponds to a predetermined electroencephalogram signal pattern.

8. An apparatus for obtaining an electroencephalogram during magnetic resonance imaging, comprising:
a plurality of nonmagnetic electrodes for receiving electroencephalogram signals from a patient;
an amplifier;
first electrical connection means for electrically connecting the plurality of electrodes to an input of the amplifier;
means for recording the electroencephalogram signals; and
second electrical connection means for electrically connecting the recording means to an output of the amplifier.

9. An apparatus for obtaining an electroencephalogram during magnetic resonance imaging as defined in claim 8, wherein the first electrical connection means comprises a plurality of electrode extension cables having a length sufficient to prevent distortion of the magnetic resonance imaging.

10. An apparatus for obtaining an electroencephalogram during magnetic resonance imaging as defined in claim 9, wherein the first electrical connection means comprises a plurality of electrode extension cables having a length of at least five centimeters.

11. An apparatus for obtaining an electroencephalogram during magnetic resonance imaging as defined in claim 9, wherein the plurality of electrode extension cables are sufficiently long that the amplifier can be positioned outside a bore of a magnet of a magnetic resonance imaging machine when the plurality of electrodes are affixed to the head of a patient positioned in the magnetic resonance imaging machine.

12. An apparatus for obtaining an electroencephalogram during magnetic resonance imaging as defined in claim 8, wherein the plurality of electrodes comprise surface electrodes having a surface of gold or silver.

13. An apparatus for obtaining an electroencephalogram during magnetic resonance imaging as defined in claim 8, wherein the plurality of electrodes comprise sphenoidal electrodes comprising silver wire.

14. An apparatus for obtaining an electroencephalogram during magnetic resonance imaging as defined in claim 8, wherein the recording means comprises an electroencephalograph machine.

15. An apparatus for obtaining an electroencephalogram during magnetic resonance imaging as defined in claim 8, wherein the recording means comprises a personal computer.

16. An apparatus for obtaining an electroencephalogram during magnetic resonance imaging as defined in claim 8, wherein the second electrical connection means comprises cable sufficiently long that the recording means can be positioned outside a magnetic resonance imaging room when the plurality of electrodes are affixed to the head of a patient positioned in a magnetic resonance imaging machine.

17. An apparatus for obtaining an electroencephalogram during magnetic resonance imaging as defined in claim 8, wherein the second electrical connection means comprises a signal splitter; and wherein the recording means comprises an electroencephalograph machine and a personal computer.

18. An apparatus for obtaining an electroencephalogram during magnetic resonance imaging as defined in claim 8, wherein the recording means comprises means for triggering a magnetic resonance imaging machine in response to a selected electroencephalogram signal pattern.

19. An apparatus for obtaining an electroencephalogram during magnetic resonance imaging, comprising:
a plurality of nonmagnetic electrodes for receiving electroencephalogram signals from a patient;
a multiplexor;
a plurality of cables electrically connected to the plurality of electrodes and to an input of the multiplexor;
an amplifier, wherein an input of the amplifier is electrically connected to an output of the multiplexor;
a signal splitter;
means for electrically connecting an output of the amplifier to an input of the signal splitter;
a demultiplexor having a plurality of outputs, wherein an input of the demultiplexor is electrically connected to a first output of the signal splitter;
an electroencephalograph machine electrically connected to the plurality of outputs of the demultiplexor; and
a signal processor having an input electrically connected to a second output of the signal splitter, wherein the signal processor comprises means for generating a signal to trigger a magnetic resonance imaging machine in response to a selected electroencephalogram signal pattern.

20. A medical diagnostic apparatus comprising:
a magnetic resonance imaging machine;
a device for recording electroencephalograph signals operated simultaneously with the magnetic resonance imaging machine;
means for transmitting a plurality of electroencephalogram signals from a patient undergoing magnetic resonance imaging to the device for recording electroencephalograph signals; and means responsive to the plurality of electroencephalogram signals for triggering the magnetic resonance imaging machine when a predetermined pattern of electroencephalogram signals is received.

21. The medical diagnostic apparatus of claim 20, wherein the magnetic resonance imaging machine is a Siemens 1.5T whole body scanner.

22. A method for obtaining metabolic information correlated to particular neurophysiological waveforms within a brain, comprising the steps of:

preparing a measurement system to perform magnetic resonance imaging while preventing interference with diagnostic quality of the magnetic resonance imaging;

continuously monitoring electroencephalogram data from the brain;

comparing the electroencephalogram data to electroencephalogram characteristics representing the particular neurophysiological waveforms;

triggering a magnetic resonance imaging in response to electroencephalogram data comparable to the particular neurophysiological waveforms; and performing the magnetic resonance imaging.

23. The method of claim 22 wherein the step of preparing a measurement system comprises the steps of:

placing a patient in a magnetic resonance imaging room;

placing a plurality of non-magnetic electrodes on the patient's head; and transmitting electroencephalogram signals from the plurality of non-magnetic electrodes to a monitoring device.

24. The method of claim 22, wherein the step of continuously monitoring includes the step of receiving signals on an electroencephalogram.

25. The method of claim 22, wherein the step of continuously monitoring includes the step of receiving signals on a computer.

26. The method of claim 22 wherein the step of comparing includes the step of a computer analyzing signals transmitted from non-magnetic electrodes.

27. The method of claim 22 wherein the step of comparing includes the step of an operator monitoring the electroencephalogram data.

28. The method of claim 22 wherein the step of triggering includes the step of a computer transmitting a signal to a magnetic resonance imaging machine when the computer receives signals comparable to the particular neurophysiological waveforms.

29. The method of claim 22 wherein the step of triggering includes the step of an operator watching a display of the electroencephalogram data and activating a magnetic resonance imaging machine when signals comparable to the particular neurophysiological waveforms appear on the display.

30. The method of claim 22, wherein the step of performing includes performing the magnetic resonance imaging with a Siemens 1.5T whole body scanner.

31. An apparatus with means for obtaining metabolic information correlated to particular neurophysiological waveforms within a brain, comprising:

a magnetic resonance imaging machine capable of measuring metabolic information;

means for continuously monitoring electroencephalogram data from the brain;

means for preventing interference with diagnostic quality of magnetic resonance imaging of the magnetic resonance imaging machine; and means for triggering magnetic resonance imaging in response to electroencephalogram data corresponding to the particular neurophysiological waveforms.

32. The apparatus of claim 31, wherein the magnetic resonance imaging machine is a Siemens 1.5T whole body scanner.

33. The apparatus of claim 31 wherein the means for continuously monitoring comprises an electroencephalogram machine.

34. The apparatus of claim 31 wherein the means for continuously monitoring comprises a computer.

35. The apparatus of claim 31 wherein the means for preventing interference with diagnostic quality comprises an electrocardiogram machine with connection to electrodes placed on a patient.

36. The apparatus of claim 31 wherein the means for triggering a magnetic resonance imaging comprises a computer with first connection to electroencephalogram electrodes and second connection to a magnetic resonance imaging machine.

* * * * *

US005445162C1

(12) EX PARTE REEXAMINATION CERTIFICATE (5029th)

United States Patent
Ives

(10) Number: US 5,445,162 C1
(45) Certificate Issued: Nov. 30, 2004

(54) APPARATUS AND METHOD FOR RECORDING AN ELECTROENCEPHALOGRAM DURING MAGNETIC RESONANCE IMAGING

(75) Inventor: John R. Ives, Lexington, MA (US)

(73) Assignee: Beth Israel Hospital Association, Brookline, MA (US)

Reexamination Request:
No. 90/005,810, Sep. 5, 2000

Reexamination Certificate for:
Patent No.: 5,445,162
Issued: Aug. 29, 1995
Appl. No.: 08/113,785
Filed: Aug. 27, 1993

(51) Int. Cl.$^7$ .............................................. A61B 5/0478
(52) U.S. Cl. ...................................... 600/544; 600/413
(58) Field of Search ................................ 600/544, 410, 600/411

(56) References Cited

U.S. PATENT DOCUMENTS

| 4,736,751 A | * | 4/1988 | Gevins et al. | 600/545 |
| 5,239,265 A | * | 8/1993 | Sugahara | 600/410 |
| 5,352,979 A | * | 10/1994 | Conturo | 324/307 |
| 5,436,564 A | * | 7/1995 | Kreger et al. | 600/411 |

OTHER PUBLICATIONS

The EEG Handbook, Craib et al., (1973).
Electrodes and the Measurement of Bioelectric Events, Geddes (1972).
Electroencephalography, Bates et al., 1963.
Bioelectricity, Suckling, 1961.
Bioelectric Recording Techniques, Thompson et al., 1974.
Electrophysiological Technique, Dickinson, 1950.

* cited by examiner

Primary Examiner—Ruth S. Smith

(57) ABSTRACT

A method and apparatus for recording an electroencephalogram (EEG) during magnetic resonance imaging (MRI). Nonmagnetic electrodes are attached to a patient's scalp. EEG signals are multiplexed, amplified, and transmitted to an EEG machine or a personal computer located outside the MRI room. By reducing the amount of magnetic metal and radio frequency generating equipment associated with the recording of the EEG that is within the bore of the MRI magnet, and moving all significant radio frequency generating equipment outside the MRI room, EEG signals can be recorded and MRI images can be obtained simultaneously. The EEG signals are analyzed and, in response to a predetermined pattern, the MRI machine is triggered.

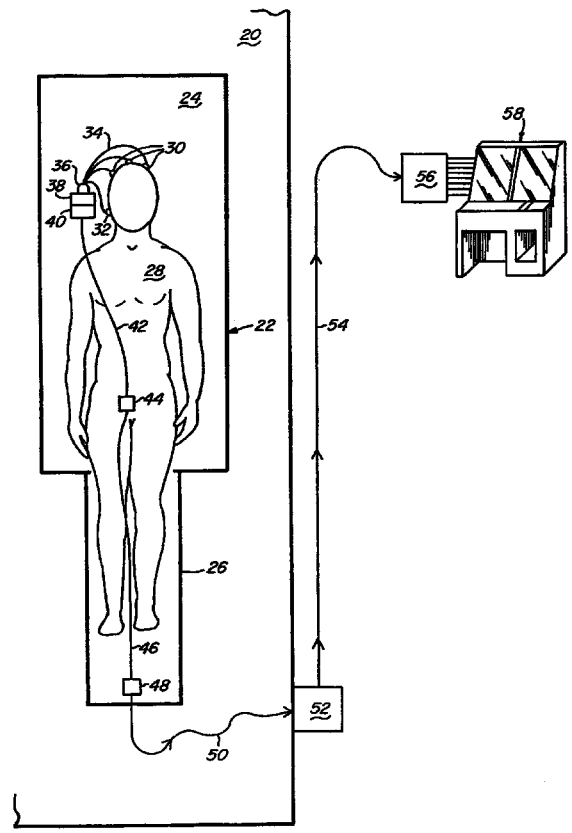

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 22–36 is confirmed.

Claims 1, 3–6 and 8–18 are cancelled.

Claims 2, 7, 19 and 20 are determined to be patentable as amended.

Claim 21, dependent on an amended claim, is determined to be patentable.

New claims 37–43 are added and determined to be patentable.

2. A method for obtaining an electroencephalogram during magnetic resonance imaging [as defined in claim 1,] *of a patient positioned in a magnetic resonance imaging room, comprising the steps of:*

*placing a plurality of nonmagnetic electrodes on the patient's head so as to be able to record the patient's electroencephalogram;*

*transmitting electroencephalogram signals from the plurality of electrodes to an amplifier; and*

*recording the amplified electroencephalogram signals;*

*wherein the step of transmitting electroencephalogram signals from the plurality of electrodes to an amplifier is performed during the magnetic resonance imaging of the patient;* wherein the recording step is conducted within the magnetic resonance imaging room.

7. A method for obtaining an electroencephalogram during magnetic resonance imaging [as defined in claim 1,] *of a patient positioned in a magnetic resonance imaging room, comprising the steps of:*

*placing a plurality of nonmagnetic electrodes on the patient's head so as to be able to record the patient's electroencephalogram;*

*transmitting electroencephalogram signals from the plurality of electrodes to an amplifier; and*

*recording the amplified electroencephalogram signals;*

*wherein the step of transmitting electroencephalogram signals from the plurality of electrodes to an amplifier is performed during the magnetic resonance imaging of the patient;* further comprising the steps of:

analyzing the recorded signals to determine an electroencephalogram signal pattern; and triggering a magnetic resonance imaging machine when the electroencephalogram signal pattern corresponds to a predetermined electroencephalogram signal pattern.

19. An apparatus for obtaining an electroencephalogram during magnetic resonance imaging, comprising:

a plurality of nonmagnetic electrodes for receiving electroencephalogram signals from a patient;

a multiplexor;

a plurality of cables electrically connected to the plurality of electrodes and to an input of the multiplexor;

an amplifier, wherein an input of the amplifier is electrically connected to an output of the multiplexor;

a signal splitter;

means for electrically connecting an output of the amplifier to an input of the signal splitter;

a demultiplexor having a plurality of outputs, wherein an input of the demultiplexor is electrically connected to a first output of the signal splitter;

an electroencephalograph machine electrically connected to the plurality of outputs of the demultiplexor *to record the electroencephalogram during the magnetic resonance imaging*; and a signal processor having an input electrically connected to a second output of the signal splitter, wherein the signal processor comprises means for generating a signal to trigger a magnetic resonance imaging machine in response to a selected electroencephalogram signal pattern.

20. A medical diagnostic apparatus comprising:

a magnetic resonance imaging machine;

a device for recording electroencephalograph signals operated simultaneously with the magnetic resonance imaging machine;

means for transmitting a plurality of electroencephalogram signals from a patient undergoing magnetic resonance imaging to the device for recording electroencephalograph signals, *the means for transmitting including a plurality of nonmagnetic electrodes*; and means responsive to the plurality of electroencephalogram signals for triggering the magnetic resonance imaging machine when a predetermined pattern of electroencephalogram signals is received.

*37. An apparatus for obtaining an electroencephalogram during magnetic resonance imaging comprising:*

*a plurality of nonmagnetic electrodes for receiving electroencephalogram signals from a patient;*

*an amplifier;*

*first electrical connection means for electrically connecting the plurality of electrodes to an input of the amplifier;*

*means for recording the electroencephalogram signals during the magnetic resonance imaging; and*

*second electrical connection means for electrically connecting the recording means to an output of the amplifier;*

*wherein the recording means comprises an analog electroencephalograph machine.*

*38. The apparatus of claim 19, wherein the electroencephalograph machine utilizes analog technology.*

39. The apparatus of claim 19, wherein the signal processor includes a comparator that compares the selected electroencephalogram signal pattern to a signal pattern provided by the second output of the signal splitter to trigger the magnetic resonance imaging machine.

40. The medical diagnostic apparatus of claim 20, wherein the device for recording electroencephalograph signals utilizes analog technology.

41. The medical diagnostic apparatus of claim 20, wherein the means for triggering the magnetic resonance imaging machine includes a comparator that compares the plurality of electroencephalogram signals to the predetermined pattern of electroencephalogram signals.

42. The apparatus of claim 31, wherein the means for continuously monitoring comprises an electroencephalograph machine utilizing analog technology.

43. The apparatus of claim 31, wherein the means for triggering magnetic resonance imaging includes a comparator that compares the electroencephalogram data from the brain to the particular neurophysiological waveforms.

* * * * *